United States Patent
Helm et al.

(10) Patent No.: US 12,211,221 B2
(45) Date of Patent: Jan. 28, 2025

(54) SYSTEMS AND METHODS FOR ENHANCEMENT OF 3D IMAGERY AND NAVIGATION VIA INTEGRATION OF PATIENT MOTION DATA

(71) Applicant: Medtronic Navigation, Inc., Louisville, CO (US)

(72) Inventors: Patrick A. Helm, Milton, MA (US); Robert J. Pahl, Broomfield, CO (US)

(73) Assignee: Medtronic Navigation, Inc., Lafayette, CO (US)

( * ) Notice: Subject to any disclaimer, the term of this patent is extended or adjusted under 35 U.S.C. 154(b) by 287 days.

(21) Appl. No.: 17/649,776

(22) Filed: Feb. 2, 2022

(65) Prior Publication Data

US 2022/0284602 A1 Sep. 8, 2022

Related U.S. Application Data

(60) Provisional application No. 63/157,956, filed on Mar. 8, 2021.

(51) Int. Cl.
*G06T 7/00* (2017.01)
*A61B 34/20* (2016.01)
(Continued)

(52) U.S. Cl.
CPC ............... *G06T 7/30* (2017.01); *A61B 34/20* (2016.02); *A61B 90/39* (2016.02); *A61B 2034/2055* (2016.02)

(58) Field of Classification Search
CPC ............ G06T 7/30; G06T 2207/10081; G06T 2207/30204; G06T 7/33; G06T 2207/10088; G06T 2207/30004; A61B 34/20; A61B 90/39; A61B 2034/2055; A61B 90/37; A61B 2034/2048; A61B 2034/2051; A61B 2034/2063; A61B 2090/374; A61B 2090/3762
See application file for complete search history.

(56) References Cited

U.S. PATENT DOCUMENTS

| 10,702,188 B2 | 7/2020 | Addison et al. |
| 2009/0046906 A1 | 2/2009 | Wohlgemuth et al. |

(Continued)

FOREIGN PATENT DOCUMENTS

| CA | 3050809 A1 | 9/2018 |
| EP | 3408832 A1 | 12/2018 |

OTHER PUBLICATIONS

International Search Report and Written Opinion corresponding to PCT/US2022/070888, Dated Jun. 7, 2022.
(Continued)

*Primary Examiner* — Md K Talukder
(74) *Attorney, Agent, or Firm* — Harness, Dickey & Pierce, P.L.C.

(57) ABSTRACT

Devices, systems, and methods used to register medical image data with anatomical positions are disclosed. The image data is captured by an imaging system over a period of time. The positions are determined by one or more modalities over the period of time. The positions are collected into position data, and determinations are made as to which position data is best for registering the image data with patient anatomy and for reconstructing 3D images of the patient anatomy.

20 Claims, 4 Drawing Sheets

(51) Int. Cl.
    *A61B 90/00*     (2016.01)
    *G06T 7/30*     (2017.01)

(56) References Cited

U.S. PATENT DOCUMENTS

| | | |
|---|---|---|
| 2011/0123083 A1* | 5/2011 | Ojha .................... G01R 33/46 |
| | | 382/131 |
| 2014/0094694 A1 | 4/2014 | Moctezuma de la Barrera |
| 2018/0046875 A1* | 2/2018 | Caluser ................ A61B 6/584 |
| 2019/0209046 A1 | 7/2019 | Addison et al. |
| 2019/0246954 A1* | 8/2019 | Adler, Jr. .............. G16H 50/50 |
| 2019/0366124 A1 | 12/2019 | Berlinger |
| 2020/0046302 A1 | 2/2020 | Jacquel et al. |
| 2020/0187827 A1 | 6/2020 | Addison et al. |
| 2022/0284602 A1* | 9/2022 | Helm .................... A61B 34/20 |
| 2023/0008051 A1 | 1/2023 | Vilsmeier et al. |

OTHER PUBLICATIONS

International Preliminary Report on Patentability with Written Opinion of the International Searching Authority (EPO), corresponding to PCT/US2022/070888, Date of Mailing Sep. 21, 2023 (9 pages).
T E Marchant et al, "Reduction of motion artefacts in on-board cone beam CT by warping of projection images", British Journal of Radiology, vol. 84, No. 999, Mar. 1, 2011, pp. 251-274.
A Review of Ultrasound and Computed Tomography Registration Approaches—2014 (Year: 2014).
Reduction of motion artefacts in on-board cone beam CT by warping of projection images—2011 (Year: 2011).
Orientation and Interpretation of CT Images—1983 (Year: 1983).

\* cited by examiner ously to U.S. Provisional Application No. 63/157,956, filed on Mar. 8, 2021 and titled "Systems And Methods for Enhancement of 3D Imagery And Navigation Via Integration of Patient Motion Data" which is hereby incorporated by reference in its entirety.

SYSTEMS AND METHODS FOR ENHANCEMENT OF 3D IMAGERY AND NAVIGATION VIA INTEGRATION OF PATIENT MOTION DATA

RELATED APPLICATIONS

This application claims priority to U.S. Provisional Application No. 63/157,956, filed on Mar. 8, 2021 and titled "Systems And Methods for Enhancement of 3D Imagery And Navigation Via Integration of Patient Motion Data" which is hereby incorporated by reference in its entirety.

TECHNICAL FIELD

The present disclosure relates generally to devices, systems, and methods used in the field of medical imagery. More specifically, the present disclosure relates to devices, systems, and methods used to register medical image data.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
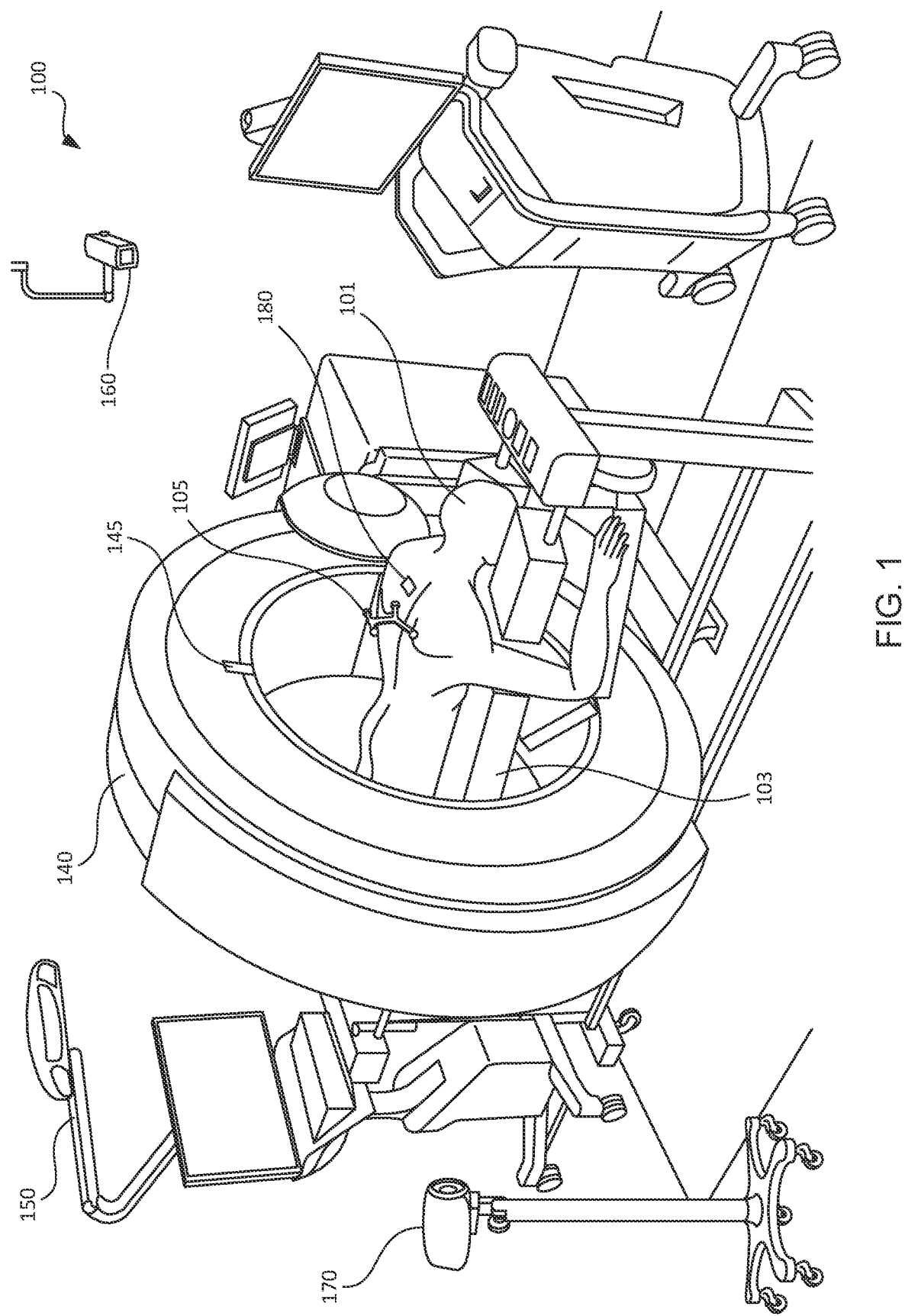
FIG. 1 is a perspective view of an operating room with an imaging system collecting image data of patient anatomy and multiple modalities determining position data of the patient anatomy in accordance with one embodiment.

Medical imagery of the anatomy of a patient can assist surgeons while operating on the patient during a surgical procedure. The imagery can help a surgeon visualize pertinent anatomical structures and accurately place surgical instruments during the procedure. An imaging system captures images of the patient's internal anatomy, such as cross-sectional views of the patient's organs.

Before a surgical procedure begins, the surgical team might capture a pre-operative imaging scan of the patient's anatomy using a medical imaging system. The imaging system can be a tomographic system, such as a magnetic resonance imaging (MRI) system or a computed tomography (CT) system. Often, the scan is taken while the patient lies on an operating table. In some embodiments, the imaging system encircles the patient about an axis and collects scanned image data from different angles around the patient. This image data is constructed into images, such as cross-sectional images of the patient's anatomy.

A medical imagery scan can be performed over a period of time. During the period of time of the scan, an array of image data is collected from multiple viewpoints corresponding to various points in time throughout the period of time of the scan.

After the scan is complete, the image data may be registered with the patient anatomy based on a position or positions of the anatomy during the period of time of the scan. Registration involves determining a coordinate transform that maps the image data into an appropriate coordinate system to overlay the image data over a current image of the patient for navigation by the surgeon. Navigation includes the process of identifying a pose (e.g., location and orientation) of a particular anatomical structure and/or of a surgical instrument.

During registration of image data with patient anatomy, the pose of the anatomy provides a basis for determining the coordinate transform used to convert the image data into the appropriate coordinate system. Ordinarily, the pose selected for registration is the initial pose of the patient anatomy at the outset of the scan. During the scan, however, the pose of the patient anatomy relative to the imaging system can change. Causes of such change include vibration of the imaging system and movement of the patient. Changes in pose may cause errors in the registration process that can be deleterious for navigation and ultimately for the surgical procedure.

Errors in registration are problematic because they cause the navigational and imagery information to be misaligned with the actual anatomy of the patient. For example, the surgeon might place an instrument in a particular location based on what the surgeon sees displayed on the display device. But the perceived pose of the patient anatomy may be different from the actual pose of the patient anatomy, leading to misplacement of the surgical instrument. Misplacement of instruments can cause serious injuries in surgery, even if the registration errors are small. Thus, it is desirable to enhance registration by using a registration position that decreases these errors.

Movement of a patient can comprise different types of motion. As one example, the foam of the operating table may compress, causing most or all of the patient's body to drift further into the table. Motion that substantially comprises movement of the patient's entire body is called bulk motion. As another example, one part of the patient's body may move during a scan relative to another part of the patient's body. For instance, while the patient breathes, the patient's chest cavity and/or back may move up and down, while other body parts such as the patient's head may remain substantially motionless relative to the chest motion. As a further instance, the patient's overall heart may experience only small changes in shape and size while it beats, whereas the internal cavities of the patient's heart may change in shape and size significantly. These kinds of localized movement of patient anatomy are called deformation. Deformation may cause one registration that is optimal for one part of the body to be suboptimal for another part. It can be advantageous, therefore, to monitor deformations of patient anatomy, and carry out multiple registrations that correspond with different anatomies of the body.

Monitoring localized deformations of different body parts and overall bulk motion of the patient's body can be done using multiple modalities for detecting patient motion. A modality can include a sensor, a detector, an observer, or a transceiver that observes movement of patient anatomy during the pre-operative scan. The modality can record the observations of anatomical movement it in the form of position data—also called motion data—and transmit them to a processor for registration. Therefore, each modality can capture a set of position data and all the sets of position data can be aggregated into overall position data.

The processor, upon receiving the position data, may evaluate the data for its fitness for use in the registration and 3D image reconstruction processes. The processor may identify and correct inaccuracies in the image data using the position data. For example, this evaluation may include determining whether one modality's set of position data is inaccurate or erratic compared to the rest of the position data. The evaluation may be based on validation criteria for establishing the accuracy of each of the modalities. If the processor determines that a set of position data is inaccurate, erratic, noisy, corrupted, or otherwise unsuited for use, the processor might omit that set of position data from the registration process.

As described above, the processor might perform multiple registrations corresponding with different anatomical parts of the body. The processor might determine that one modality is best suited for performing registration on a local level at a particular anatomical structure, while a different modality is best suited for registration at a whole-body level or at a different local anatomy. Further, the processor might use position data from more than one modality for registration, selecting one modality as a chief modality on which to base the registration, and supplementing the registration with the additional position data from the other modality or modalities.

Embodiments herein may improve the registration process by collecting the position data during the scan and using the position data to determine a more accurate pose of the patient anatomy in the pre-operative scan on which to base the registration. Position data can comprise a displacement between the patient anatomy and the imaging system. Rather than base the registration on a pose determined before or at the beginning of the scan, the registration can be accomplished based on a pose or poses that is or are determined during the scan. For example, an average position of the patient anatomy can be calculated from the position data collected during the scan. Using that average position for the pose inputted into the registration process may improve the results of the registration, and consequently, navigation. Using multiple modalities can further enhance the accuracy of registration by collecting additional position data and utilizing the strengths of the various modalities.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While various aspects of the embodiments are presented in drawings, the drawings are not necessarily drawn to scale unless specifically indicated.

FIG. 1 depicts a perspective view of an imaging and position tracking system 100. Within an operating room is an operating table 103, on which a patient 101 lies. Before a surgical procedure begins, an imaging system 140 is positioned around the patient 101 to run a scan and collect imagery (e.g., a pre-operative scan) of the patient's anatomy. A combination of multiple modalities may be used to monitor the scene and observe the movements of the patient 101. Examples of modalities include tracking systems, three-dimensional (3D) cameras, radiofrequency (RF) modules, ultrasonic transducers, electromagnetic technologies, inertial sensors, and the imaging system 140 itself.

A tracking system 150 may be used to observe the movements of a patient tracker 105 and of an imaging system tracker 145. The tracking system 150 may determine relative positions throughout the scan between the patient tracker 105 and the imaging system tracker 145. The relative positions between the patient tracker 105 and the imaging system tracker 145 can be converted into relative positions between the patient anatomy and the imaging system 140. Such conversion may be based on known positional relationships between the imaging system 140 and the imaging system tracker 145, and between the patient anatomy and the patient tracker 105.

The tracking system 150 can be an image guidance system. An image guidance system uses optical technology to detect and monitor the poses of various trackers. In particular, the image guidance system can detect a patient tracker 105, an instrument tracker, and an imaging system tracker 145.

A patient tracker 105 is a device that the surgeon couples to the patient 101. The patient tracker 105 can be a reference frame. A reference frame can be a rigid object with distinct surfaces on it that can be detected by the tracking system 150. The reference frame can rest on the body of the patient 101, be coupled to a clamp used by the surgeon to restrain the patient 101 during the procedure, or be coupled to the patient 101 in some other way. The tracking system 150 determines poses of the reference frame in three-dimensional space. Determination of poses of the reference frame can happen throughout the period of time of the scan, as well as after the scan during the surgical procedure. These poses may be included in an array of position data collected and stored by the tracking system 150.

An instrument tracker is a device coupled to or part of a surgical instrument. It can be a rigid object with distinct surfaces for detection by the tracking system 150, similar to the patient tracker 105. The tracking system 150 determines poses of the instrument tracker in three-dimensional space during the surgical procedure.

In addition to detecting a patient tracker 105 coupled to the patient 101 and an instrument tracker coupled to a surgical instrument, the tracking system 150 can detect an imaging system tracker 145 embedded within or coupled to the imaging system 140. The tracking system 150 can determine poses of the imaging system tracker 145 in three-dimensional space throughout the period of time of a preoperative scan. To do this, the tracking system 150 can employ a similar method to that used to detect and track the patient tracker 105.

The tracking system 150 can detect and track the poses of the patient tracker 105 and the imaging system tracker 145 throughout the duration of the scan. The poses of these trackers can be compared with each other to determine relative positions of the patient tracker 105 to the imaging system tracker 145.

The relative positions of the patient tracker 105 and the imaging system tracker 145 may be recorded. An array of these positions of the patient tracker 105 relative to the imaging system 140 can be determined throughout the duration of the scan. Such an array of relative positions may be part of the position data determined by the tracking system 150.

Additional modalities 160, 170, 180 may include 3D cameras, RF modules, ultrasonic transducers, electromagnetic technologies, and inertial sensors.

A 3D camera may be mounted to the imaging system 140. 3D cameras may be located elsewhere in the operating room. An array of two-dimensional cameras may be used to provide three-dimensional images. The 3D camera(s) may be configured to observe whole patient motion, such as bulk motion. The 3D camera(s) may be configured to observe localized regions of interest, including deformation. For example, a 3D camera might observe a breathing pattern of a patient 101 and collect motion data in the form of a breathing motion waveform. The 3D camera(s) and/or the imaging and position tracking system 100 may employ image recognition software to observe specific points on the patient anatomy and determine motion of those points over time.

An RF module may be located in the operating room. The RF module(s) may be a radiofrequency receiver or transceiver that detects radiofrequency echoes from off of the patient 101. The RF module(s) may be configured to observe bulk motion. The RF module(s) may be configured to observe deformation. The radiofrequency waves may be millimeter waves.

An ultrasonic transducer may be placed in the operating room at a distance from the patient, as in modality 170, or in contact with the patient, as in modality 180. The ultrasonic transducer may detect localized motion, such as deformation of the chest and organs within the chest. An array of ultrasonic transducers may be used to overcome obstacles that would otherwise block a single ultrasound signal. For example, an array of ultrasonic transducers may be placed around the chest or back of a patient 101 to overcome blocking of ultrasonic signals by the patient's ribs. An ultrasound detector, or an array of ultrasound detectors, may be embedded in the operating table 103. Ultrasound detectors may be located on an opposite side of the patient 101 from the ultrasonic transducer(s). The ultrasound detectors may sense ultrasound waves emitted from the ultrasonic transducer(s) and augment the position data determined by the ultrasonic transducer(s). The ultrasonic transducer(s) may comprise a piezoelectric transducer. The ultrasonic transducer(s) may comprise a capacitive transducer, such as a capacitive micromachined ultrasonic transducer.

An inertial sensor or sensors may be coupled to the body of a patient 101, as in modality 180, to detect movements of patient anatomy. The inertial sensor(s) may include a single-axis accelerometer, a two-axis accelerometer, or a three-axis accelerometer, to detect translational motion. The inertial sensor(s) may include a gyroscope or gyroscopes to detect rotational motion. The inertial sensor(s) may comprise microelectromechanical systems (MEMS). The motion data from the inertial sensor(s) may include a magnitude and direction of movement, including velocity and/or acceleration. Multiple inertial sensors may be used to gather motion data of multiple anatomies or multiple points on a patient anatomy. The inertial sensors may be configured to detect bulk motion. The inertial sensors may be positioned strategically to detect deformations in a region of interest.

Additional modalities may include video-based monitoring of vital signs as described in U.S. Pat. No. 10,702,188 (SYSTEM AND METHODS FOR VIDEO-BASED MONITORING OF VITAL SIGNS); non-contact video monitoring to measure tidal volume of a patient as described in US Publication No. 2019/0209046 (SYSTEMS AND METHODS FOR VIDEO-BASED NON-CONTACT TIDAL VOLUME MONITORING); video systems for non-contact detecting and monitoring of patient breathing as described in US Publication No. US 2020/0046302 (VIDEO-BASED PATIENT MONITORING SYSTEMS AND ASSOCIATED METHODS FOR DETECTING AND MONITORING BREATHING); and systems for non-contact detecting and monitoring of patient breathing as described in US Publication No. US 2020/0187827 (DEPTH SENSING VISUALIZATION MODES FOR NON-CONTACT MONITORING), each of which are incorporated by referenced herein in their entirety.

An additional method for augmenting position data is to use fiducial markers. A fiducial marker may be an object having a distinct characteristic, such as a distinct shape or surface, which may be trackable by the imaging system 140 or another modality. Fiducial markers may be placed on a patient 101 to aid other modalities in detecting patient motion. For example, the patient tracker 105 may comprise a fiducial marker that is tracked by the tracking system 150. As another example, the imaging system 140 may detect a fiducial maker coupled to the patient 101 and record position data of the fiducial marker during the period of time that the imaging system 140 collects image data. The position data of the fiducial marker may be incorporated into the position data of the patient anatomy, and be used to determine movements of the patient anatomy where the fiducial marker is located.

The position data may include the poses of patient anatomies during the pre-operative scan. The position data may include displacements between the patient anatomy and the imaging system 140. The position data may include displacements between the patient anatomy and other modalities. The position data may include displacements between the patient anatomy and some reference point or datum within the operating room. The position data may include displacements between the imaging system 140 and some reference point or datum within the operating room. The position data can include both translational and rotational displacements. It can include other states such as velocities. It can be represented in any of various coordinate systems. For example, the position data can include data in Cartesian coordinate form, spherical coordinate form, Euler angle form, direction cosine form, quaternion form, and/or other forms.

The position data can be used to transform the image data into a coordinate system that corresponds with the live imagery of a patient that the surgeon sees on a display device during the surgical procedure. This process is known as registration. Registration is the determination of a mapping between the coordinates in one space and those in another (e.g., a pre-operative scan and live imagery of a patient during an operation), such that points in the two spaces that correspond to the same anatomical point are mapped to each other. For example, the imaging system may map a pre-operative scan and live imagery of a patient during an operation to overlay the pre-operative scan on a graphical user interface. The registration process may include determining a coordinate transform that maps the image data and the position data into a uniform coordinate system in order to properly reconstruct the imagery and provide navigational information to the surgeon.

Navigation may include the method used by the surgeon to track the poses of the patient anatomy and the surgical instruments. During a surgical procedure, an instrument can be tracked in an object or subject space. In various embodiments the subject space can be a patient space defined by a patient 101. The location of the instrument that is tracked can be displayed on the display device relative to an image of the patient 101. The surgeon can track an instrument relative to the patient 101 based upon the registered image data, where the tracking system 150 tracks the instrument and an icon representing the instrument is super-imposed on the image seen by the surgeon.

A problem that surgeons encounter while registering image data with patient anatomy is noise in the image data. A common source of noise is movement within the operating room that negatively affects the image data during a scan. For example, the imaging system 140 can vibrate, which causes the equipment in the imaging system 140, such as transceivers or detectors, to vibrate and consequently to blur the data collected. As another example of a source of noise in the image data, the patient can move during a scan. One type of patient motion is from breathing. With air entering and exiting the patient's lungs, the patient's chest or back will move up and down. This can be particularly problematic during a scan of the patient's spine, for example, because even millimeter movements of the spine can lead to incorrect navigational information based on the image data. Another type of motion of the patient can be from voluntary or involuntary movement of a part of the body during the scan. For example, in a procedure in which the patient is awake, the patient's head may move from side to side by several millimeters. These kinds of motions add noise to the image data and can have significant adverse consequences on registration, navigation, and 3D image reconstruction. When the image data collected by the imaging system is noisy, the navigational information to the surgeon can contain undesirable errors. For example, if the position of the patient during a pre-operative scan is not what is expected, the registration process may cause the overlay of the pre-operative scan during surgery to be off which may provide the surgeon with incorrect navigation data. Additionally, the reconstructed 3D images can be blurry.

The navigational errors and blurry images resulting from noise in the position data can be mitigated by using multiple modalities for collecting the position data. Additional modalities provide additional motion data from measurements of patient movement, which increases the accuracy of registration. The imaging and position tracking system might determine weights for position data from the various modalities based on known or learned properties of the modalities that indicate accuracy and precision of the sensing capabilities of the modalities.

Embodiments herein may identify and correct inaccuracies in the image data using the position data. When modalities are combined, their various time scales and spatial scales can be used to the advantage of better registration. For example, if a first modality operates at 1 Hz with high accuracy, and a second modality operates at 2 Hz with medium accuracy, the imaging and position tracking system might give great weight to the position data collected every second by the first modality, and less weight to the corresponding-in-time position data collected by the second modality. Meanwhile, the imaging and position tracking system might fully incorporate into the registration process the additional position data from the second modality collected at the half-second increments when the first modality does not collect data. As another example, a first modality might capture patient motion data at high accuracy on a localized spatial scale to specific anatomy, while a second modality might capture patient motion data at medium accuracy on a full-body spatial scale. The imaging and position tracking system might incorporate all of the motion data from both modalities, but give greater weight to the first modality at the space on and around the specific anatomy. This can increase the accuracy of registration for the specific anatomy, while still allowing for registration of image data of the whole body or of a larger spatial scale.

A further advantage of combining modalities is that registration can be enhanced by selecting a best modality and its associated coordinate system on which to base the registration process. One method of selecting a best coordinate system for registration is to designate tiers for each modality based on known properties of the modalities prior to the imaging scan. For example, the imaging system 140 might be designated as first tier, the tracking system 150 might be designated as second tier, and additional modalities might be designated as third tier, fourth tier, etc. In this case, the registration process would use the coordinate system of the imaging system 140 so long as the imaging system 140 is tracking position data properly. If not, the registration process would use the coordinate system of the next tiered modality. Another method of selecting a best coordinate system for registration is to adaptively or dynamically determine which coordinate system is best. Under this approach, the various modalities could have their tiers dynamically reassigned based on validation criteria that tests the accuracy or other quality of the various modalities. Criteria for accuracy testing may include comparisons of collected position data with expected results or a noise threshold. Other criteria for accuracy testing may include comparisons of collected position data of one modality with collected position data of other modalities. If a certain modality's position data is erratic in light of other position data, the imaging and position tracking system may redetermine that modality's tier with a lower value.

Another advantage of using more than one modality for observing patient motion is that a plurality of modalities provides redundancy. If a modality is determined to have erratic or corrupted data, the registration and 3D image reconstruction processes can rely on the other modalities to provide the necessary position data.

Figure 2:
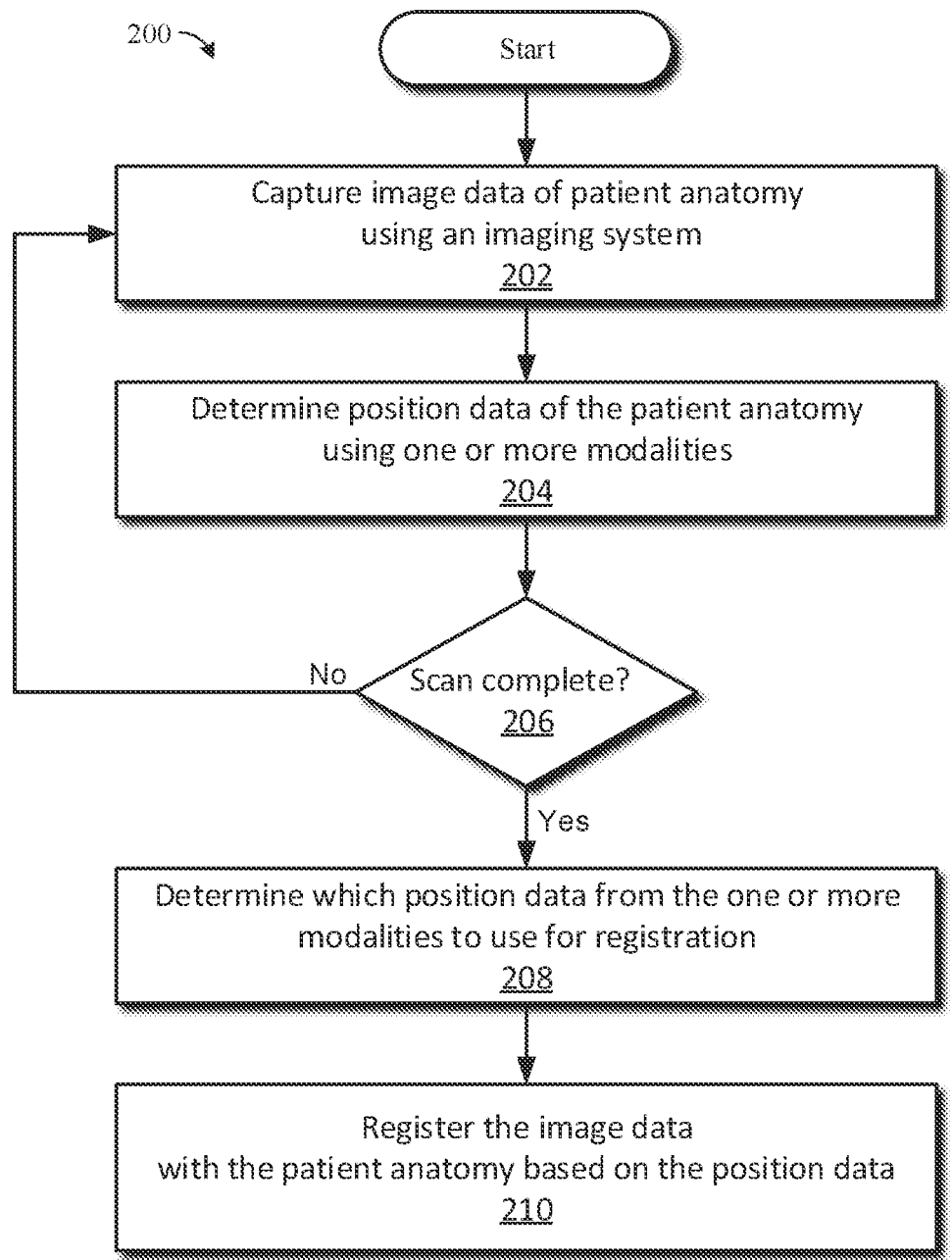
FIG. 2 is a flow chart of a method for registering image data with patient anatomy in accordance with one embodiment.

FIG. 2 is a flow chart of a method 200 for registering image data with patient anatomy based on position data. The method 200 may be used by an imaging and position tracking system such as shown in FIG. 1. The method 200 may begin with a scan carried out by an imaging system. During the scan, an imaging system may capture 202 image data of patient anatomy.

Concurrently with the imagery capture, one or more modalities may determine 204 position data of the patient anatomy. The position data may include the pose of the patient anatomy relative to the imaging system. The position data may include the pose of the patient anatomy relative to one or more other modalities. The position data may include the pose of the patient anatomy with respect to a fixed reference datum in the operating room. The position data may include the pose of the imaging system relative to a fixed reference datum in the operating room. The position data may include the pose of the other modalities relative to a fixed reference datum in the operating room.

Each modality of the one or more modalities may determine 204 position data and collect it into a separate set of position data. In other words, a first modality may determine 204 a first set of position data, a second modality may determine 204 a second set of position data, etc. The various sets of position data may be aggregated into one overall collection of position data for use by the imaging and position tracking system.

The position data of the patient anatomy may be updated based on position data of the imaging system. As discussed above, the position data determined by the one or more modalities may include poses of the imaging system relative to a fixed reference datum in the operating room. If the imaging system moves during the scan, for example due to vibration, the movement of the imaging system may be captured and reflected in the position data that includes the poses of the imaging system. This position data of the imaging system may be used to update the position data of the patient anatomy. For example, the poses of patient anatomy relative to the imaging system may be combined with the poses of the imaging system relative to the reference datum to enhance the position data of patient anatomy, including determining or updating poses of patient anatomy relative to the fixed reference datum.

In some embodiments, the one or more modalities includes a tracking system. A tracking system may comprise an image guidance system that optically tracks a pose of a patient tracker relative to a position of the imaging system. For example, a tracking system may identify and track an imaging system tracker coupled to the imaging system and a patient tracker coupled to the patient. The tracking system may determine position data based on locations of the imaging system tracker and locations of the patient tracker during the period of time.

Image data may be repeatedly captured 202 and position data may be repeatedly determined 204 until the imaging scan is completed 206.

After completion 206 of the scan, the imaging and position tracking system may determine 208 which position data from the one or more modalities to use for registration. The determination 208 of which position data to use for registration may be based on a hierarchy of tiers of the various modalities. The modality with the highest tier—the chief modality—may be the best choice for determining a coordinate system on which to base the registration. Additionally, the imaging and position tracking system may judge the position data sets determined by the other modalities against the position data set determined by the chief modality to assess the quality and/or accuracy of the other modalities' position data sets. The imaging and position tracking system may compare an individual position data set against one or more other position data set to assess its quality and/or accuracy. These comparisons may be based on validation criteria for determining whether a position data set is inaccurate, corrupted, overly noisy, or otherwise untrustworthy.

The imaging and position tracking system may combine more than one position data set to determine a position or positions of patient anatomy on which to base registration. This combination may use a weighting method to determine how to prioritize the position data sets and/or how much influence a particular position data set should have on registration. The weighting method may be based on the hierarchy of tiers of the various modalities. The combination of more than one position data set may utilize the differing time and spatial scales of the various modalities. For example, if a first modality is optimal for a narrow view of a patient's chest, that first modality might be the chief modality for registration of anatomy in the patient's chest. If a second modality is optimal for a wide view of bulk patient motion, that second modality might be the chief modality for registration of whole-patient anatomy.

The hierarchy of tiers of the various modalities may be adaptively or dynamically determined. For example, if an expected hierarchy of tiers of the various modalities is not borne out to be accurate during a scan of image data or after a scan is complete, the imaging and position tracking system may update the tier designations based on analysis of the position data collected during the scan. This analysis may be based on validation criteria.

After determining 208 which position data from the one or more modalities to use for registration, the imaging and position tracking system may register 210 the image data with the patient anatomy based on the position data. The imaging and position tracking system may identify and correct inaccuracies in the image data using the position data. Identification of patient motion via the position data may be performed independently of registration or at the same time as registration. For example, in some embodiments a post-registration process may be performed where registration occurs and then the corrections to the image data are added after the registration is complete. In some embodiments, the imaging and position tracking system may identify and correct inaccuracies caused by patient before registration happens. The corrections may be used to provide a more accurate image and provide a more accurate registration.

The imaging and position tracking system may compute a position value or values of patient anatomy to be used in the registration process. As there can be multiple anatomies for which a registration will be performed, there can be multiple position values. Additionally, there can be multiple registrations for a patient anatomy at differing times during the period of time of the scan, thus requiring multiple position values for a particular anatomy. The following discussion about a position value of patient anatomy is generally applicable to multiple position values, whether they be across points in time or for different anatomies.

A position value of the patient anatomy may be determined from—and incorporated into—the position data. The imaging and position tracking system may use the position value as part of a registration procedure. The position value may be an average position. For example, the imaging and position tracking system may determine an average position of the patient anatomy over the scan duration.

In some embodiments, averaging the position data may be carried out by taking the average value of an array of poses of the patient anatomy relative to the imaging system that correspond with an array of time data associated with the period of time of the scan. In some embodiments, the averaging can be done with respect to each component of pose (including each component of, for example, location and orientation) in the coordinate frame by which the position data is stored. In some embodiments, the averaging may be done with respect to only certain of the components of pose in the coordinate frame by which the position data is stored. In some embodiments, the averaging may be done in a different coordinate system than the one by which the position data is stored. In some embodiments, the averaging can comprise using an arithmetic mean. In some embodiments, the averaging can comprise using a geometric mean. In some embodiments, the averaging can include integrating the position data over the period of time of the scan.

In some embodiments, the averaging may be done with respect to a magnitude or other norm of the position data. In some embodiments, the averaging may comprise an unconventional averaging process. In some embodiments, the averaging may comprise a weighting method. A weighting method may include a time-weighted or a position-weighted calculation. For example, the averaging process may give special weight to position data collected near the beginning time and the end time of the pre-operative scan, and may give less weight to position data collected near the middle of the scan's duration. As another example, the averaging process may give special weight to location values corresponding with less erratic orientation values, and may deemphasize location values corresponding with orientation values deviating greatly from an expected or calculated orientation of anatomy. The averaging process may comprise an iterative calculation process that successively updates the weights of the weighting method and refines the position data.

Based on the position data, the image data may be registered 210 with the patient anatomy. More specifically, the registration 210 can be based on a position value, such as an average position of the patient anatomy. After the array of poses of patient anatomy is averaged to determine an average position, the average position can be used to register 210 the image data with the patient anatomy. This is in contrast with using a predetermined pose that the imaging and position tracking system determines before the scan is run. The predetermined pose would ordinarily be detected at the outset of the scan, but it might be an outlier among the various actual poses throughout the scan. The average position can better represent the actual poses of the patient anatomy for purposes of registration and image reconstruction. Determining the average position of a patient anatomy—and more generally, determining the position data of the patient anatomy—can be enhanced by using multiple modalities in the imaging and position tracking system.

Figure 3:
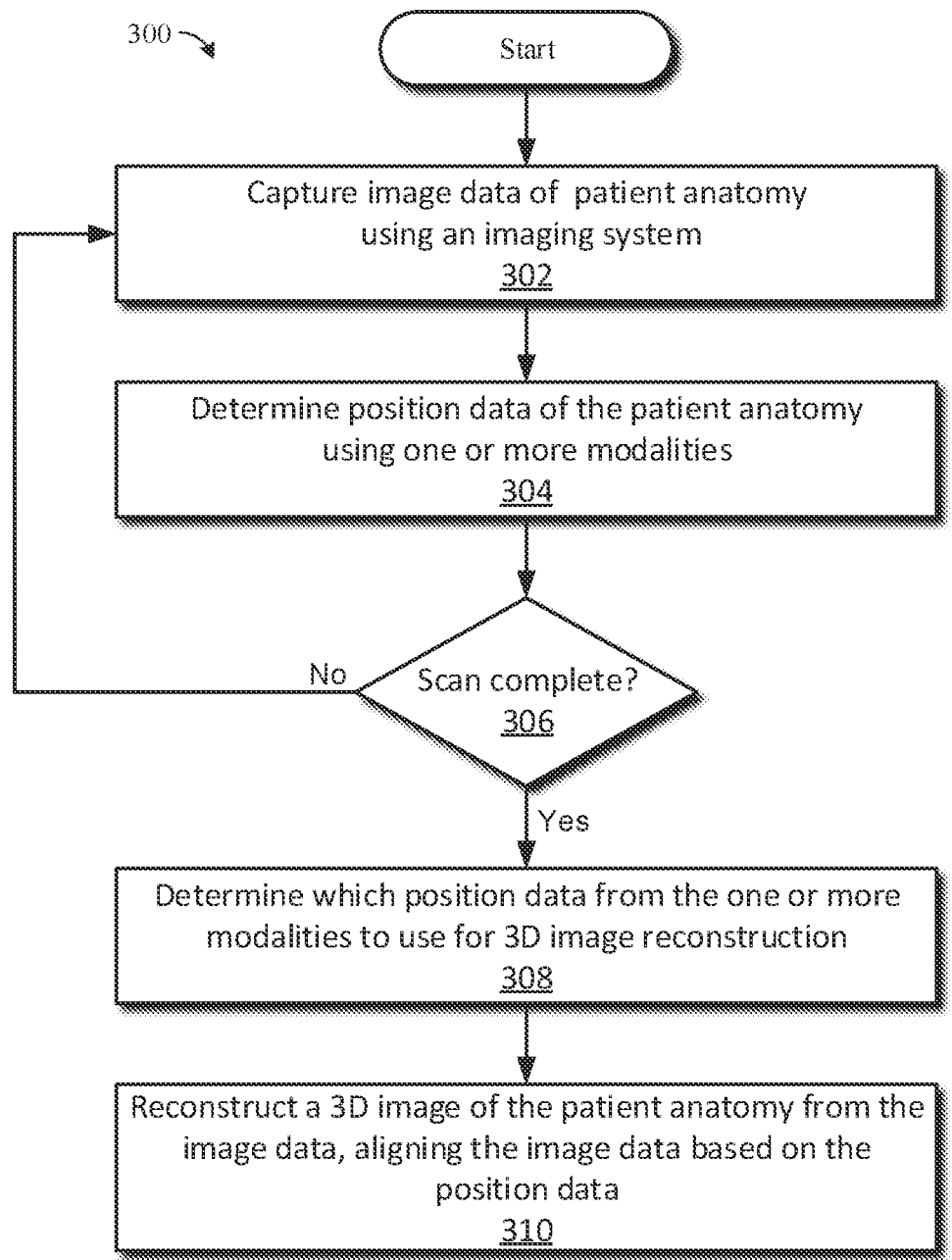
FIG. 3 is a flow chart of a method for reconstructing a three-dimensional (3D) image of patient anatomy in accordance with one embodiment.

FIG. 3 is a flow chart of a method 300 for reconstructing a 3D image of patient anatomy. The method 300 may be used by an imaging and position tracking system such as shown in FIG. 1. The method 300 may begin with a scan carried out by an imaging system. During the scan, the imaging system may capture 302 image data of patient anatomy.

Concurrently with the imagery capture, one or more modalities may determine 304 position data of the patient anatomy. The position data may include the pose of the patient anatomy relative to the imaging system. The position data may include the pose of the patient anatomy relative to one or more other modalities. The position data may include the pose of the patient anatomy with respect to a fixed reference datum in the operating room. The position data may include the pose of the imaging system relative to a fixed reference datum in the operating room. The position data may include the pose of the other modalities relative to a fixed reference datum in the operating room.

Each modality of the one or more modalities may determine 304 position data and collect it into a separate set of position data. In other words, a first modality may determine 304 a first set of position data, a second modality may determine 304 a second set of position data, etc. The various sets of position data may be aggregated into one overall collection of position data for use by the imaging and position tracking system.

The position data of the patient anatomy may be updated based on position data of the imaging system. As discussed above, the position data determined by the one or more modalities may include poses of the imaging system relative to a fixed reference datum in the operating room. If the imaging system moves during the scan, for example due to vibration, the movement of the imaging system may be captured and reflected in the position data that includes the poses of the imaging system. This position data of the imaging system may be used to update the position data of the patient anatomy. For example, the poses of patient anatomy relative to the imaging system may be combined with the poses of the imaging system relative to the reference datum to enhance the position data of patient anatomy, including determining or updating poses of patient anatomy relative to the fixed reference datum.

In some embodiments, the one or more modalities includes a tracking system. A tracking system may comprise an image guidance system that optically tracks a pose of a patient tracker relative to a position of the imaging system. For example, a tracking system may identify and track an imaging system tracker coupled to the imaging system and a patient tracker coupled to the patient. The tracking system may determine position data based on locations of the imaging system tracker and locations of the patient tracker during the period of time.

Image data may be repeatedly captured 302 and position data may be repeatedly determined 304 until the imaging scan is completed 306.

After completion 306 of the scan, the imaging and position tracking system may determine 308 which position data from the one or more modalities to use for 3D image reconstruction. The determination 308 of which position data to use for 3D image reconstruction may be based on a hierarchy of tiers of the various modalities. The modality with the highest tier—the chief modality—may be the best choice for determining a coordinate system on which to base the 3D image reconstruction. Additionally, the imaging and position tracking system may judge the position data sets determined by the other modalities against the position data set determined by the chief modality to assess the quality and/or accuracy of the other modalities' position data sets. The imaging and position tracking system may compare an individual position data set against one or more other position data set to assess its quality and/or accuracy. There comparisons may be based on validation criteria for determining whether a position data set is inaccurate, corrupted, overly noisy, or otherwise untrustworthy.

The imaging and position tracking system may combine more than one position data set to determine a position or positions of patient anatomy on which to base 3D image reconstruction. This combination may use a weighting method to determine how to prioritize the position data sets and/or how much influence a particular position data set should have on 3D image reconstruction. The weighting method may be based on the hierarchy of tiers of the various modalities. The combination of more than one position data set may utilize the differing time and spatial scales of the various modalities. For example, if a first modality is optimal for a narrow view of a patient's chest, that first modality might be the chief modality for 3D image reconstruction of anatomy in the patient's chest. If a second modality is optimal for a wide view of bulk patient motion, that second modality might be the chief modality for 3D image reconstruction of whole-patient anatomy.

The hierarchy of tiers of the various modalities may be adaptively or dynamically determined. For example, if an expected hierarchy of tiers of the various modalities is not borne out to be accurate during a scan of image data or after a scan is complete, the imaging and position tracking system may update the tier designations based on analysis of the position data collected during the scan. This analysis may be based on validation criteria.

After determining 308 which position data from the one or more modalities to use for 3D image reconstruction, the imaging and position tracking system may reconstruct 310 a 3D image of the patient anatomy from the image data, aligning the image data based on the position data. The imaging and position tracking system may compute a position value or values of patient anatomy to be used in the 3D image reconstruction process. As there can be multiple anatomies for which a 3D image reconstruction will be performed, there can be multiple position values. Additionally, there can be multiple 3D image reconstructions for a patient anatomy at differing times during the period of time of the scan, thus requiring multiple position values for a particular anatomy. The following discussion about a position value of patient anatomy is generally applicable to multiple position values, whether they be across points in time or for different anatomies.

A position value of the patient anatomy may be determined from—and incorporated into—the position data. The imaging and position tracking system may use the position value as part of a 3D image reconstruction procedure. The imaging and position tracking system may align the image data based on the position value. In some embodiments, the position value may be an average position. For example, the imaging and position tracking system may determine an average position of the patient anatomy over the scan duration.

In some embodiments, averaging the position data may be carried out by taking the average value of an array of poses of the patient anatomy relative to the imaging system that correspond with an array of time data associated with the period of time of the scan. In some embodiments, the averaging can be done with respect to each component of pose (including each component of, for example, location and orientation) in the coordinate frame by which the position data is stored. In some embodiments, the averaging may be done with respect to only certain of the components of pose in the coordinate frame by which the position data is stored. In some embodiments, the averaging may be done in a different coordinate system than the one by which the position data is stored. In some embodiments, the averaging can comprise using an arithmetic mean. In some embodiments, the averaging can comprise using a geometric mean. In some embodiments, the averaging can include integrating the position data over the period of time of the scan.

In some embodiments, the averaging may be done with respect to a magnitude or other norm of the position data. In some embodiments, the averaging may comprise an unconventional averaging process. In some embodiments, the averaging may comprise a weighting method. A weighting method may include a time-weighted or a position-weighted calculation. For example, the averaging process may give special weight to position data collected near the beginning time and the end time of the pre-operative scan, and may give less weight to position data collected near the middle of the scan's duration. As another example, the averaging process may give special weight to location values corresponding with less erratic orientation values, and may deemphasize location values corresponding with orientation values deviating greatly from an expected or calculated orientation of anatomy. The averaging process may comprise an iterative calculation process that successively updates the weights of the weighting method and refines the position data.

Using the average position of patient anatomy determined after the scan can reduce blurriness of the 3D images that are reconstructed 310 from the image data. It can also increase the accuracy of navigation during the surgical procedure. While at some increments of time during the scan, the average position may be farther from some of the actual poses than a predetermined pose would be, other actual poses during the scan may be better represented by the average position, and on the whole, the average position may be better suited for registration and 3D image reconstruction than the predetermined pose. The average position may reduce the magnitude of the error caused by movement of the patient or imaging system. Determining the average position of a patient anatomy—and more generally, determining the position data of the patient anatomy—can be enhanced by using multiple modalities in the imaging and position tracking system.

Figure 4:
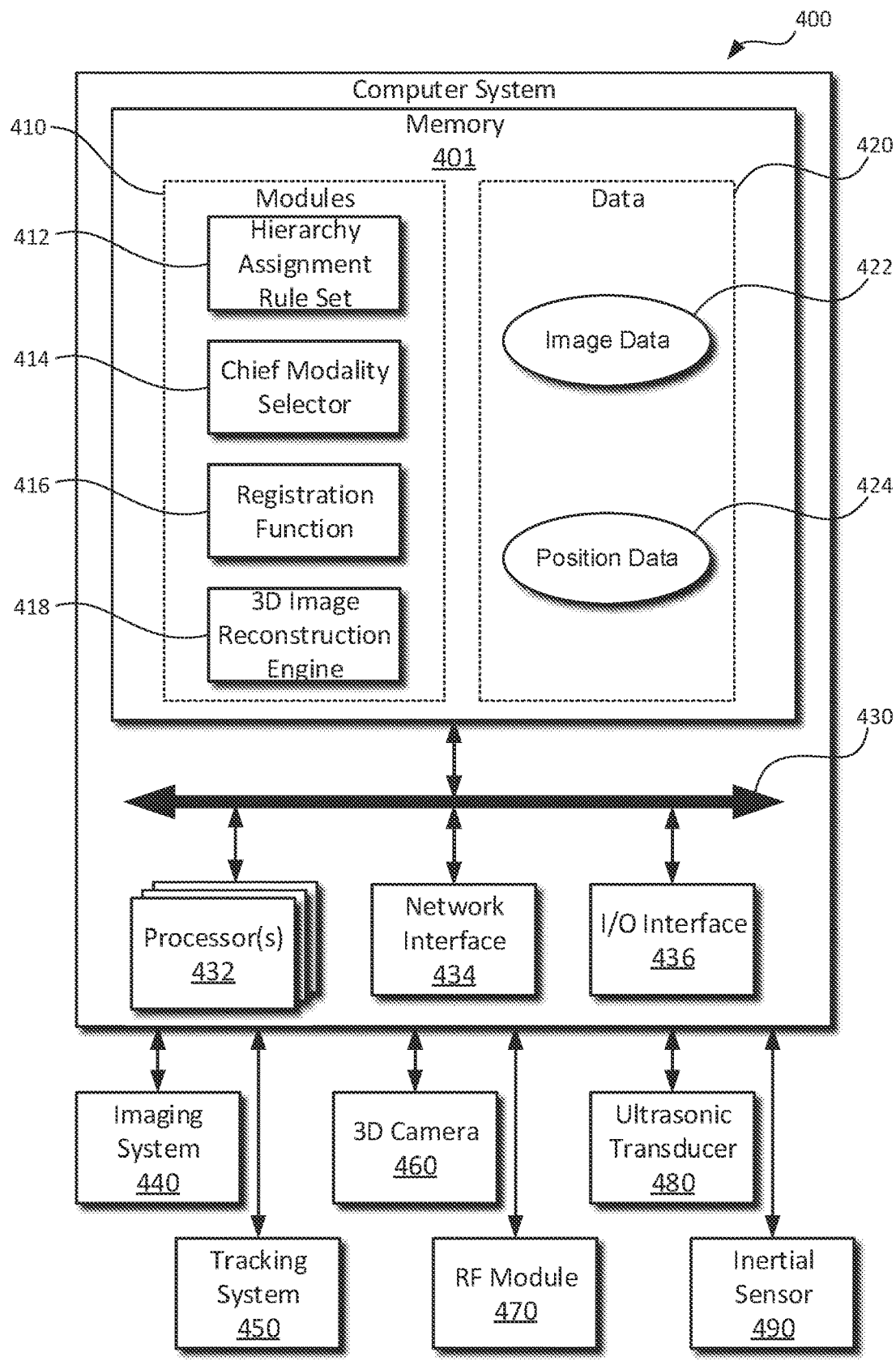
FIG. 4 is a block diagram of a computing system configured for registration and 3D image reconstruction in accordance with one embodiment.

FIG. 4 is a block diagram of a computing system 400 configured for registration and 3D image reconstruction. The computing system 400 can comprise a computing apparatus that includes memory 401, one or more processors 432, a network interface 434, an input/output interface 436, and a system bus 430.

The one or more processors 432 may include one or more general purpose devices, such as a standard microprocessor. The one or more processors 432 may include a special purpose processing device, such as ASIC, SoC, SiP, FPGA, PAL, PLA, FPLA, PLD, or other customized or programmable device. The one or more processors 432 can perform distributed (e.g., parallel) processing to execute or otherwise implement functionalities of the presently disclosed embodiments. The one or more processors 432 may run a standard operating system and perform standard operating system functions. It is recognized that any standard operating system may be used.

The memory 401 may include static RAM, dynamic RAM, flash memory, one or more flip-flops, ROM, CD-ROM, DVD, disk, tape, or magnetic, optical, or other computer storage mediums. The memory 401 may include a plurality of program modules 410 and program data 420. The memory 401 may be local to the computing system 400, as shown, or may be distributed and/or remote relative to the computing system 400.

The memory 401 may include the program data 420. Data generated or used by the computing system 400, such as by the program modules 410 or other modules, may be stored on the memory 401, for example, as stored program data 420. The program data 420 may be organized as one or more databases. The program data 420 may include image data 422 collected by an imaging system 440 and position data 424 collected by a plurality of modalities. The plurality of modalities may include the imaging system 440, a tracking system 450, a three-dimensional camera 460, a radiofrequency module 470, an ultrasonic transducer 480, and an inertial sensor 490. The plurality of modalities may include multiples of each of said modalities. The position data 424 may comprise the distance between a tracker on a patient and a tracker on the imaging system 440 over a duration of a scan. The position data 424 may comprise multiple sets of position data determined and collected by the plurality of modalities.

The program modules 410 may include all or portions of other elements of the computing system 400. The program modules 410 may run multiple operations concurrently or in parallel by or on the one or more processors 432. In some embodiments, portions of the disclosed modules, components, and/or facilities are embodied as executable instructions embodied in hardware or firmware, or stored on a non-transitory, machine-readable storage medium. The executable instructions may comprise computer program code that, when executed by a processor and/or computing device, cause a computing system to implement certain processing steps, procedures, and/or operations, as disclosed herein. The modules, components, and/or facilities disclosed herein may be implemented and/or embodied as a driver, a library, an interface, an API, FPGA configuration data, firmware (e.g., stored on an EEPROM), and/or the like. In some embodiments, portions of the modules, components, and/or facilities disclosed herein are embodied as machine components, such as general and/or application-specific devices, including, but not limited to: circuits, integrated circuits, processing components, interface components, hardware controller(s), storage controller(s), programmable hardware, FPGAs, ASICs, and/or the like. Accordingly, the modules disclosed herein may be referred to as controllers, layers, services, engines, facilities, drivers, circuits, subsystems, and/or the like. The program modules 410 may comprise a hierarchy assignment rule set 412, a chief modality selector 414, a registration function 416, and a 3D image reconstruction engine 418. The hierarchy assignment rule set 412 may provide a basis for determining the tiers of the plurality of modalities. The chief modality selector 414 may select the chief modality for providing a coordinate system for registration and 3D image reconstruction. The selection may be based on the operation of the plurality of modalities in accordance with the hierarchy assignment rule set 412. The registration function 416 may use the position data 424 to register the image data 422. The 3D image reconstruction engine 418 may use the position data 424 to compile the image data 422 into a 3D image. For example, the position data 424 may be used to align the image data 422.

The input/output interface 436 may facilitate user interaction with one or more input devices and/or one or more output devices. The input device(s) may include a keyboard, mouse, touchscreen, light pen, tablet, microphone, sensor, or other hardware with accompanying firmware and/or software. The output device(s) may include a monitor or other display, printer, speech or text synthesizer, switch, signal line, speaker, or other hardware with accompanying firmware and/or software. In some embodiments, the input/output interface 436 is a touchscreen.

The network interface 434 may facilitate communication with other computing devices and/or networks and/or other computing and/or communications networks. The network interface 434 may be equipped with conventional network connectivity, such as, for example, Ethernet (IEEE 1102.3), Token Ring (IEEE 1102.5), Fiber Distributed Datalink Interface (FDDI), or Asynchronous Transfer Mode (ATM). Further, the network interface 434 may be configured to support a variety of network protocols such as, for example, Internet Protocol (IP), Transfer Control Protocol (TCP), Network File System over UDP/TCP, Server Message Block (SMB), Common Internet File System (CIFS), Hypertext Transfer Protocols (HTTP), Direct Access File System (DAFS), File Transfer Protocol (FTP), Real-Time Publish Subscribe (RTPS), Open Systems Interconnection (OSI) protocols, Simple Mail Transfer Protocol (SMTP), Secure Shell (SSH), Secure Socket Layer (SSL), and so forth.

The system bus 430 may facilitate communication and/or interaction between the other components of the computing system 400, including the one or more processors 432, the memory 401, the input/output interface 436, and the network interface 434.

EXAMPLE SECTION

The following Examples pertain to further embodiments.

Example 1

A method for registering image data with anatomy of a patient, the method comprising: capturing, via an imaging system, image data of patient anatomy for a period of time; determining, via a plurality of modalities, position data of the patient anatomy during the period of time that the image data is being captured; and correcting inaccuracies in the image data using the position data.

Example 2

A method according to Example 1, further comprising registering the image data with the patient anatomy based on the position data of the patient anatomy determined by one or more of the plurality of modalities.

Example 3

A method according to Example 1, wherein the plurality of modalities are selected from one or more of an optical tracking system, a three-dimensional camera, radiofrequency modules, ultrasonic transducers, and inertial sensors.

Example 4

A method according to Example 1, further comprising detecting, via the imaging system, locations of a fiducial marker during the period of time, wherein the fiducial marker is coupled to the patient.

Example 5

A method according to Example 4, wherein the locations of the fiducial marker detected during the period of time are incorporated into the position data of the patient anatomy used to register the image data with the patient anatomy.

Example 6

A method according to Example 1, further comprising determining, via the plurality of modalities, position data of the imaging system during the period of time that the image data is being captured, and updating the position data of the patient anatomy based on the position data of the imaging system.

Example 7

A method according to Example 1, further comprising designating tiers to the imaging system and each of the plurality of modalities, such tiers defining a hierarchy of tiers of modalities.

Example 8

A method according to Example 7, wherein the designation of tiers is dynamically updated during or after the period of time that the image data is being captured.

Example 9

A method according to Example 7, further comprising selecting a chief modality from the imaging system and each of the plurality of modalities based on the hierarchy of tiers of modalities, such chief modality providing a coordinate system for registering the image data with the patient anatomy.

Example 10

A method according to Example 1, wherein the registering of the image data with the patient anatomy is based on the position data of the patient anatomy determined by more than one of the plurality of modalities.

Example 11

A method according to Example 1, wherein a first modality is used to observe bulk motion of patient anatomy and a second modality is used to observe deformations of patient anatomy.

Example 12

A method according to Example 1, wherein selection of which of the plurality of modalities to use for registering the image data with the patient anatomy is based on validation criteria for establishing accuracy of each of the plurality of modalities.

Example 13

A method according to Example 1, further comprising reconstructing a 3D image of the patient anatomy from the image data and the position data of the patient anatomy.

Example 14

A method according to Example 13, wherein the position data of the patient anatomy is used to align the image data.

Example 15

A system comprising: a first modality configured to capture a first set of position data of patient anatomy; a second modality configured to capture a second set of position data of patient anatomy; and a processor configured to: receive image data of a patient; receive the first set of position data of patient anatomy and the second set of position data of patient anatomy; and correct inaccuracies in the image data using the first set of position data of patient anatomy and the second set of position data of patient anatomy.

Example 16

A system according to Example 15, wherein the processor is further configured to register the image data with patient anatomy based on at least one of the first set of position data of patient anatomy and the second set of position data of patient anatomy.

Example 17

A system according to Example 15, wherein the plurality of modalities are selected from one or more of an optical tracking system, a three-dimensional camera, radiofrequency modules, ultrasonic transducers, and inertial sensors.

Example 18

A system according to Example 15, further comprising an imaging system configured to detect locations of a fiducial marker, wherein the fiducial marker is coupled to the patient.

Example 19

A system according to Example 15, wherein the processor is further configured to designate tiers to the first modality and the second modality, such tiers defining a hierarchy of tiers of modalities.

Example 20

A system according to Example 18, wherein the designation of tiers is dynamically updated during or after a period of time in which the image data is captured.

Example 21

A system according to Example 18, further comprising selecting a chief modality from the first modality and the second modality based on the hierarchy of tiers of modalities, such chief modality providing a coordinate system for registering the image data with the patient anatomy.

Example 22

A system according to Example 15, wherein the processor is configured to register the image data with patient anatomy based on both the first set of position data of patient anatomy and the second set of position data of patient anatomy.

Example 23

A system according to Example 15, wherein the first modality is configured to capture bulk motion of patient anatomy and the second modality is configured to capture deformations of patient anatomy.

Example 24

A system according to Example 15, wherein the processor is configured to select which of the first set of position data of patient anatomy and the second set of position data of patient anatomy to use for registration of the image data with the patient anatomy based on validation criteria for establishing accuracy of each of the first modality and the second modality.

Example 25

A system according to Example 15, wherein the processor is further configured to reconstruct a 3D image of the patient anatomy from the image data and at least one of the first set of position data of patient anatomy and the second set of position data of patient anatomy.

Example 26

A computing apparatus comprising: a processor; and memory storing instructions that, when executed by the processor, configure the apparatus to: capture, via an imaging system, image data of patient anatomy for a period of time; determine, via a plurality of modalities, position data of the patient anatomy during the period of time that the image data is being captured; and register the image data with the patient anatomy based on the position data of the patient anatomy.

Example 25

A computing apparatus according to Example 24, wherein the plurality of modalities are selected from one or more of an optical tracking system, a three-dimensional camera, radiofrequency modules, ultrasonic transducers, and inertial sensors

Example 26

A computing apparatus according to Example 24, wherein the apparatus is further configured to detect, via the imaging system, locations of a fiducial marker during the period of time, wherein the fiducial marker is coupled to the patient.

Example 27

A computing apparatus according to Example 24, wherein the apparatus is further configured to designate tiers to the imaging system and each of the plurality of modalities, such tiers defining a hierarchy of tiers of modalities.

Example 28

A computing apparatus according to Example 24, wherein the apparatus is further configured to observe bulk motion of patient anatomy via a first modality, and deformations of patient anatomy via a second modality.

Example 29

A computing apparatus according to Example 24, wherein the apparatus is further configured to reconstruct a 3D image of the patient anatomy from the image data and the position data of the patient anatomy.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A method for registering image data with anatomy of a patient, the method comprising:
    capturing, via an imaging system, image data of patient anatomy for a period of time;
    determining, via a plurality of different modalities, position data of the patient anatomy during the period of time that the image data is being captured;
    designating tiers to the imaging system and each of the plurality of different modalities, such tiers defining a hierarchy of tiers of modalities; and
    correcting inaccuracies in the image data using the position data.

2. The method according to claim 1, further comprising registering the image data with the patient anatomy based on the position data of the patient anatomy determined by one or more of the plurality of different modalities.

3. The method according to claim 1, wherein the plurality of different modalities are selected from one or more of an optical tracking system, a three-dimensional camera, radiofrequency modules, ultrasonic transducers, and inertial sensors.

4. The method according to claim 1, further comprising detecting, via the imaging system, locations of a fiducial marker during the period of time, wherein the fiducial marker is coupled to the patient, wherein the locations of the fiducial marker detected during the period of time are incorporated into the position data of the patient anatomy used to register the image data with the patient anatomy.

5. The method according to claim 1, further comprising determining, via the plurality of different modalities, position data of the imaging system during the period of time that the image data is being captured, and updating the position data of the patient anatomy based on the position data of the imaging system.

6. The method according to claim 1, wherein the designation of tiers is dynamically updated during or after the period of time that the image data is being captured.

7. The method according to claim 1, further comprising selecting a chief modality from the imaging system and each of the plurality of different modalities based on the hierarchy of tiers of modalities, such chief modality providing a coordinate system for registering the image data with the patient anatomy.

8. The method according to claim 1, wherein a first modality is used to observe bulk motion of patient anatomy and a second modality is used to observe deformations of patient anatomy.

9. The method according to claim 2, wherein selection of which of the plurality of different modalities to use for registering the image data with the patient anatomy is based on validation criteria for establishing accuracy of each of the plurality of different modalities.

10. The system according to claim 1, wherein the position data is an average position value of the patient anatomy.

11. The system according to claim 10, wherein the average position value is based upon averaging each component of pose.

12. The system according to claim 11, wherein each component of pose includes location and orientation.

13. A system comprising:
a first modality configured to capture a first set of position data of patient anatomy;
a second modality configured to capture a second set of position data of patient anatomy; and
a processor configured to:
receive image data of a patient;
receive the first set of position data of patient anatomy and the second set of position data of patient anatomy; and
correct inaccuracies in the image data using the first set of position data of patient anatomy and the second set of position data of patient anatomy;
wherein the processor is further configured to designate tiers to the first modality and the second modality, such tiers defining a hierarchy of tiers of modalities.

14. The system according to claim 13, wherein the processor is further configured to register the image data with patient anatomy based on at least one of the first set of position data of patient anatomy and the second set of position data of patient anatomy.

15. The system according to claim 13, wherein the first and second modalities are selected from one or more of an optical tracking system, a three-dimensional camera, radiofrequency modules, ultrasonic transducers, and inertial sensors.

16. The system according to claim 14, further comprising selecting a chief modality from the first modality and the second modality based on the hierarchy of tiers of modalities, such chief modality providing a coordinate system for registering the image data with the patient anatomy.

17. The system according to claim 13, wherein the processor is configured to select which of the first set of position data of patient anatomy and the second set of position data of patient anatomy to use for registration of the image data with the patient anatomy based on validation criteria for establishing accuracy of each of the first modality and the second modality.

18. The system according to claim 13, wherein the processor is further configured to reconstruct a 3D image of the patient anatomy from the image data and at least one of the first set of position data of patient anatomy and the second set of position data of patient anatomy.

19. A computing apparatus comprising:
a processor; and
memory storing instructions that, when executed by the processor, configure the apparatus to:
capture, via an imaging system, image data of patient anatomy for a period of time;
determine, via a plurality of modalities, position data of the patient anatomy during the period of time that the image data is being captured; and
register the image data with the patient anatomy based on the position data of the patient anatomy;
wherein the apparatus is further configured to designate tiers to the imaging system and each of the plurality of modalities, such tiers defining a hierarchy of tiers of modalities.

20. The computing apparatus according to claim 19, wherein the plurality of modalities are selected from one or more of an optical tracking system, a three-dimensional camera, radiofrequency modules, ultrasonic transducers, and inertial sensors.

* * * * *